US010285918B2

(12) United States Patent
Cho et al.

(10) Patent No.: US 10,285,918 B2
(45) Date of Patent: May 14, 2019

(54) COSMETIC COMPOSITION

(71) Applicant: CQV CO., LTD., Jincheon-gun, Chungcheongbuk-do (KR)

(72) Inventors: Kum-Sung Cho, Jincheon-gun (KR); Min Choi, Gwangju (KR); Kwang-Choong Kang, Cheongju-si (KR); Byung-Ki Choi, Cheongju-si (KR); Kwang-Soo Lim, Cheongju-si (KR); Kil-Wan Chang, Cheongju-si (KR)

(73) Assignee: CQV CO., LTD., Jincheon-Gun, Chungcheongbuk-Do ( * ) Notice: Subject to any disclaimer, the term of this patent is extended or adjusted under 35 U.S.C. 154(b) by 0 days.

(21) Appl. No.: 15/104,145

(22) PCT Filed: Oct. 28, 2014

(86) PCT No.: PCT/KR2014/010213
§ 371 (c)(1),
(2) Date: Jun. 13, 2016

(87) PCT Pub. No.: WO2015/088137
PCT Pub. Date: Jun. 18, 2015

(65) Prior Publication Data
US 2016/0361241 A1 Dec. 15, 2016

(30) Foreign Application Priority Data
Dec. 13, 2013 (KR) .................. 10-2013-0155675

(51) Int. Cl.
| *A61K 8/19* | (2006.01) |
| *A61K 8/97* | (2017.01) |
| *A61K 8/29* | (2006.01) |
| *A61Q 1/02* | (2006.01) |
| *A61Q 1/04* | (2006.01) |
| *A61Q 1/06* | (2006.01) |
| *A61Q 1/08* | (2006.01) |
| *A61Q 1/10* | (2006.01) |
| *A61K 8/81* | (2006.01) |
| *A61Q 3/02* | (2006.01) |
| *A61K 8/02* | (2006.01) |

(52) U.S. Cl.
CPC .............. *A61K 8/19* (2013.01); *A61K 8/0266* (2013.01); *A61K 8/29* (2013.01); *A61K 8/8141* (2013.01); *A61K 8/97* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 3/02* (2013.01); *A61K 2800/43* (2013.01); *A61K 2800/436* (2013.01); *A61K 2800/622* (2013.01)

(58) Field of Classification Search
None
See application file for complete search history.

(56) References Cited

U.S. PATENT DOCUMENTS

| 4,648,908 | A | * | 3/1987 | Takasuka | A61K 8/11 106/417 |
| 2001/0014341 | A1 | | 8/2001 | Lemann et al. | |
| 2005/0167450 | A1 | | 8/2005 | Lanzendorfer et al. | |
| 2006/0280762 | A1 | * | 12/2006 | Kostick | A61K 8/97 424/401 |
| 2010/0047300 | A1 | * | 2/2010 | Kaupp | A61K 8/25 424/401 |
| 2013/0129803 | A1 | | 5/2013 | De Clermont-Gallerande et al. | |
| 2013/0216597 | A1 | | 8/2013 | Mathias et al. | |

FOREIGN PATENT DOCUMENTS

| CN | 101511947 A | 8/2009 |
| JP | 52-146436 A | 12/1977 |
| JP | 10-158537 A | 6/1998 |
| JP | 10-330637 A | 12/1998 |
| JP | 2003-55575 A | 2/2003 |
| JP | 2004-315426 A | 11/2004 |
| JP | 2008-247882 A | 10/2008 |
| JP | 2010-523511 A | 7/2010 |
| JP | 2011-127051 A | 6/2011 |
| JP | 2013-532710 A | 8/2013 |
| KR | 10-2008-0015223 A | 2/2008 |
| KR | 10-2011-0047151 A | 5/2011 |
| KR | 10-2012-0039080 A | 4/2012 |
| KR | 10-2012-0113661 A | 10/2012 |
| KR | 10-2013-0114013 A | 10/2013 |
| KR | 10-2013-0132826 A | 12/2013 |
| WO | 0155263 A1 | 8/2001 |
| WO | 2012/055507 A1 | 5/2012 |

OTHER PUBLICATIONS

International Search Report dated Jan. 30, 2015 corresponding to International Application PCT/KR2014/010213.
European Search Report dated Mar. 5, 2017 corresponding to European Application No. 14870326.7.
Japanese Office Action dated Aug. 15, 2017 in connection with the counterpart Japanese Patent Application No. 2016-539143.
Chinese Office Action dated Feb. 13, 2018 in connection with the counterpart Chinese Patent Application No. 201480068057.3.
Japanese Office Action dated Feb. 20, 2018 in connection with the counterpart Japanese Patent Application No. 2016-539143.
Yan, "Carmine Pigment May Cause Allergic Reactions", Life & Disaster, p. 18-19, May 2012.
Chinese Office Action dated Oct. 8, 2018 in connection with the counterpart Chinese Patent Application No. 201480068057.3, citing the above reference(s).

* cited by examiner

*Primary Examiner* — Nannette Holloman
(74) *Attorney, Agent, or Firm* — Hauptman Ham, LLP

(57) ABSTRACT

Disclosed is a cosmetic composition capable of exhibiting various colors, including red, yellow and blue colors. The disclosed cosmetic composition comprises a red, yellow or blue pearlescent pigment prepared by coating a natural pigment on a matrix, so that it is capable of exhibiting various colors.

10 Claims, No Drawings

COSMETIC COMPOSITION

CROSS REFERENCE TO RELATED APPLICATION

This application claims the priority of Korean Patent Application No. 10-2013-0155675, filed on Dec. 13, 2013 in the KIPO (Korean Intellectual Property Office). Further, this application is the National Phase application of International Application No. PCT/KR2014/010213 filed Oct. 28, 2014, which designates the United States and was published in Korean.

TECHNICAL FIELD

The present invention relates to cosmetic manufacturing technology, and more particularly, to a cosmetic composition containing a pearlescent pigment prepared by coating with a vegetable natural pigment.

BACKGROUND ART

Cosmetic products follow trends, and thus various cosmetic products are being continuously put on the market. Cosmetic products contain various components, including oils, pigments and resins, and among these components, the pigments determine the color of the cosmetic products.

Cosmetic products include base makeup products that are applied to all parts of the face, and point makeup products that are applied only to a portion of the face. Among these cosmetic products, the makeup products include lipsticks, eye shadows, blushers, etc., and color is the most important factor in these cosmetic products.

A raw material that has most frequently been used to date in cosmetic products to show red is carmine which is an animal red pigment obtained by drying and powdering cochineal insects parasitic on cactus plants. Carmine is widely used as a red pigment in cosmetic products, beverages, ice creams, etc. Carmine may cause allergic reactions such as hives, nasitis or asthma in some people, and may cause attention deficit hyperactivity disorder in children.

Prior art documents related to the present invention Korean Laid-Open Patent Publication No. 10-2012-0113661 (published on Oct. 15, 2012) which discloses a makeup composition containing a black mixture of pigments.

DISCLOSURE

Technical Problem

It is an object of the present invention to provide a cosmetic composition using a pearlescent pigment prepared by coating with a vegetable natural pigment capable of exhibiting various colors.

Technical Solution

To achieve the above object, in accordance with an embodiment of the present invention, there is provided a cosmetic composition containing a pigment, a resin and a solvent, wherein the pigment comprises a pearlescent pigment prepared by coating a vegetable natural pigment on a matrix, so that the cosmetic composition is capable of exhibiting various colors.

In the present invention, the pigment is preferably contained in an amount of 2-50 wt % based on the total weight of the composition.

The cosmetic composition is preferably an oily cosmetic composition in which the solvent is oil and the resin is an oil-soluble resin.

The cosmetic composition is preferably an aqueous cosmetic composition in which the solvent is water and the resin is a water-soluble resin.

Advantageous Effects

The cosmetic composition according to the present invention contains a red, yellow or blue pearlescent pigment prepared by coating a vegetable natural pigment on a matrix, and thus can exhibit red, yellow and blue colors. In addition, it may contain a mixture of pigments so as to exhibit various colors, including green, violet, pink, purple, black, white and gray colors.

MODE FOR INVENTION

Hereinafter, the cosmetic composition according to the present invention will be described in detail.

The cosmetic composition according to the embodiment of the present invention is used for the preparation of cosmetic products, including mascara, eyeshadow, liquid eyeliner, gel type eyeliner, nail enamel, foundation, lipstick, lip gloss, cosmetic cream, makeup foundation, eye pencil, blusher or emulsion, and contains a pigment, a resin and a solvent, like conventional cosmetic compositions.

The cosmetic composition according to the present invention contains a red, yellow or blue pearlescent pigment prepared by coating the vegetable natural pigment on a matrix, and thus can exhibit red, yellow and blue colors. In addition, it may contain a mixture of pigments exhibiting different colors, and thus exhibit various colors, including green, violet, pink, purple, black, white and gray colors.

A specific method for preparing the red, yellow or blue pearlescent pigment coated with the vegetable natural pigment will be described below.

The pigment may be contained in an amount of 2-50 wt % based on the total weight of the composition. If the content of the pigment in the composition is less than 2 wt %, it will be difficult to sufficiently exhibit a desired color. On the contrary, if the content of the pigment is more than 50 wt %, there will be a problem in that excessive aggregation of the pigment particles occur or the storage stability of the composition is reduced.

The cosmetic composition may be an oily cosmetic composition or an aqueous cosmetic composition. Preferably, it is an oily cosmetic composition.

If the cosmetic composition is an oily cosmetic composition, the solvent may be oil, and the resin may be an oil-soluble resin. Examples of this oil-soluble resin include ethyl cellulose, propyl cellulose, and vinyl ester copolymers, as well as various oil-soluble resins which are used for preparation of cosmetic products.

On the contrary, if the cosmetic composition is an aqueous cosmetic composition, the solvent may be water, and the resin may be a water-soluble resin. Examples of this water-soluble resin include protein, keratin, polyacrylate or polymethacrylate, polyvinylpyrrolidone, polyvinyl alcohol, etc., as well as various known water-soluble resins.

The solvent may be contained in an amount of about 10-40 wt % when the cosmetic composition is a solid cosmetic composition, and may be contained in an amount of about 50-80 wt % when the cosmetic composition is a liquid cosmetic composition, but is necessarily limited thereto. A process for preparing the cosmetic composition may include a process of removing the solvent or a process of adding the solvent.

The cosmetic composition according to the present invention may further contain various additives, including a moisturizing agent, a wetting agent, an antioxidant, an antimicrobial agent, etc.

Hereinafter, a method for preparing the pigment that is contained in the cosmetic composition according to the present invention will be described.

Method for Preparation of Natural Pigment and Method 1 for Preparation of Pearlescent Pigment Using Natural Pigment An example of a method for preparing a pearlescent pigment using a natural pigment comprises the steps of: adding an inorganic salt solution to vegetable natural dye, followed by adjustment to a pH of 5-7, thereby preparing a primary pigment (natural pigment); and mixing a matrix suspension with a pH adjusting agent and the primary pigment to form an oxide layer on the surface of the matrix, thereby preparing a pearlescent pigment. This method is more suitable when red, yellow, violet, green or black natural dye is used.

More specifically, the method for preparing the pearlescent pigment comprises the steps of: obtaining natural dye from a dye-containing material; preparing a pigment from the natural dye; adding an inorganic salt solution to the dye to form a primary pigment (natural pigment) comprising the natural dye; forming a matrix suspension by mixing in water (deionized water, distilled water, etc.) a metal oxide-coated pearlescent pigment composition and a flaky matrix comprising one or more selected from among synthetic mica, natural mice, flaky glass, flaky iron oxide, flaky alumina, flaky silica, talc, and bismuth, followed by stirring and dispersion; and mixing the matrix suspension with a pH adjusting agent and the pigment to coat an oxide layer on the surface of the flaky matrix.

The step of preparing the primary pigment (natural pigment) comprises the steps of: preparing dye from a natural dye-containing material; adding the dye to a metal salt-containing solution to prepare a dye/metal salt mixture solution; stirring the dye/metal salt mixture solution; precipitating pigment particles in the dye/metal salt mixture solution; and separating the precipitated pigment particles, followed by drying.

The step of preparing the dye comprises the steps of: adding 10-30 parts by weight of the natural dye to 100 parts by weight of distilled water or organic solvent, followed by heating, thereby extracting a dye solution; and concentrating the extracted dye solution, and drying the concentrate in a vacuum. Herein, the natural dye may be red, yellow, violet, blue, green or black natural dye.

Herein, the dye-containing material for the natural dye may be at least one red or violet material selected from among madder, safflower, *sappan* wood, logwood, gromwell, persimmon, apricot trees, plum trees, Korean spindle trees, ginger trees, radix *Euphorbiae kansui, Althaea rosea, Polygonum cuspidatum*, wild apricot trees, *Taxus cuspidata, Schizandra chinensis, camellia*, grapes, brush trees, and combinations thereof, or may be at least one yellow or green material selected from among *gardenia, Curcuma longa*, onion peels, *Carthamus* yellow, *Coptis japonica* root, *Phellodendron amurense* bark, clove, pomegranate, reed, *Sophorae flus, Fraxinus rhynchophylla, Rhus verniciflua*, old trees, *Sorbus alnifolia*, garden-bell tree bark, *wisteria* flowers, alders, chestnuts, oak trees, and combinations thereof.

The inorganic salt may be a metal salt, and the metal salt may comprise one or more selected from among $BaCl_2$, $CaCl_2$, $AlCl_3$, $SnCl_4$, $TiCl_4$, $TiOCl_2$, $TiOSO_4$, $FeCl_3$, $FeSO_4$, $SiCl_4$, $ZrOCl_2$, $Na_2O.SiO_2.5H_2O$, $MnCl_2$, $MgCl_2$ and $CoCl_2$.

The dye/metal salt mixture solution may be prepared to include 100 parts by weight of deionized water, 3-30 parts by weight of the dye, and 3-30 parts by weight of the metal salt.

Then, the dye/metal salt mixture solution is stirred. While the dye/metal salt mixture solution is heated and stirred at a temperature of 20° C. to 60° C. at a speed of 200 rpm to 300 rpm, a basic solution containing one or more selected from among NaOH, KOH, $Ca(OH)_2$, $NH_3$, $Mg(OH)_2$, $CH_3NH_2$, $CH_3CH_2NH_2$, $CH_3OH$ and $Al(OH)_3$ is added to the dye/metal salt solution to adjust the pH to 5-7 to thereby precipitate pigment particles. Herein, if the temperature is lower than 20° C., the efficiency of the reaction will be reduced, and if the temperature is higher than 60° C., the color of the pigment can be changed.

Next, the precipitated pigment particles are separated, and then dried.

The step of forming the pigment comprises the steps of: milling the pigment; and adding pigment to deionized water, followed by stirring and dispersion.

In the step of milling the pigment, the pigment is preferably sufficiently milled at a speed of 200 rpm to 500 rpm for 12-24 hours. For example, milling balls are filled in a 500 mL vessel to a volume of 300 mL. If the volume of the milling balls is smaller than 300 mL, the efficiency of the milling will be reduced, and aggregated pigment particles will not be uniformly dispersed, and if the volume of the milling balls is greater than 300 mL, the amount of pigment that can be introduced into the vessel will be smaller than the amount of the milling balls, and thus the efficiency of the milling will be reduced. The milling is performed for 12-24 hours. If the speed of the milling is lower than 200 rpm, the effect of dispersion will be reduced, and if the speed of the milling speed is higher than 500 rpm, the effect of dispersion will no longer increase, and the pigment particles will be damaged. For this reasons, for the quality of the pigment, it is important to improve the dispersion of the pigment particles at a suitable milling speed (rpm).

According to the process as described above, a primary pigment (natural pigment) can be prepared.

In order to prepare a pearlescent pigment by coating the natural pigment on a matrix, the following additional process is required.

The step of forming the matrix suspension by mixing in deionized water the metal oxide-coated pearlescent pigment composition and the flaky matrix comprising one or more selected from among synthetic mica, natural mice, flaky glass, flaky iron oxide, flaky alumina, flaky silica, talc, and bismuth, followed by stirring and dispersion, may be performed at 200-500 rpm. The matrix suspension formed in the step of forming the matrix suspension is mixed with a pH adjusting agent and the pigment to coat the surface of the flaky matrix with the pigment particles containing the vegetable natural dye component. Herein, the pH adjusting agent may be an acidic solution containing one or more selected from among hydrochloric acid, sulfuric acid, acetic acid and the like, which are acidic.

In the step of coating the flaky substrate, the pH of the mixture solution of the matrix suspension and the pigment is adjusted to 4.0-8.0, and the coating process is performed at 200-500 rpm for 30-60 minutes.

The preparation method further comprises, after the step of coating the flaky matrix, the steps of: washing and dehydrating the flaky matrix coated with the oxide layer; drying the washed flaky matrix; and screening a flaky matrix having a size larger than a desired size among the dried flaky matrix through a mesh.

The step of drying the flaky matrix may be performed at a temperature of 60° C. to 100° C. for 12-24 hours.

In the step of screening the flaky matrix, the separated flaky matrix has a particle size of 45 μm or less. In the screening step, aggregated particles formed during the reaction may be removed using a mesh.

Method 2 for Preparation of Pearlescent Pigment Using Natural Pigment

Another example of the method for preparing the pearlescent pigment using the natural pigment comprises the steps of: preparing a primary pigment from a vegetable natural material containing dye, followed by ball milling, thereby preparing a natural pigment; adding a matrix and the primary pigment to water, followed by stirring; and titrating the stirred material with an inorganic salt solution, followed by stirring, thereby forming an oxide layer on the surface of the matrix. This method is particularly preferred when blue or green dye is used.

More specifically, a method for preparing the natural pigment comprises: obtaining natural dye from a dye-containing material; preparing a pigment from blue natural dye; and adding water to the pigment, followed by stirring. In addition, a method for preparing a pearlescent pigment comprising the natural pigment coated on a matrix comprises the steps of: forming a matrix suspension by mixing a flaky matrix comprising one or more selected from among synthetic mica, natural mica, flaky glass, flaky iron oxide, flaky alumina, flaky silica, talc and bismuth, a metal oxide-coated pigment composition, the natural pigment, and deionized water, followed by stirring and dispersion; and adding an inorganic salt solution to the matrix suspension to adjust the pH, followed by stirring, thereby coating an oxide layer on the surface of the flaky matrix.

The step of preparing the pigment comprises the steps of: adding 5-30 parts by weight of the natural dye to 100 parts by weight of distilled water or organic solvent, followed by heating, thereby extracting a dye solution; and concentrating the extracted dye solution, and drying the concentrate in a vacuum. Herein, the natural dye may be blue or green natural dye.

Herein, the dye-containing material for the natural dye may be at least one blue or green material selected from among indigo, *Commelina communis*, iris, and combinations thereof.

In the ball milling step, when the amount of the deionized water is 100 parts by weight, the pigment is preferably used in an amount of 10-30 parts by weight. If the pigment is used in an amount of less than 10 parts by weight, the reaction efficiency can be reduced due to the low concentration of the pigment, and the pigment is used in an amount of more than 30 parts by weight, the reaction efficiency can be reduced because the amount of the natural pigment relative to the reaction solution is too large.

Meanwhile, in the ball milling step, the ball milling is preferably performed for 6-12 hours. If the ball milling time is shorter than 6 hours, dispersion will be insufficient, and if the ball milling time is longer than 12 hours, the process time becomes longer without a further dispersion effect, resulting in a decrease in efficiency.

According to the above-described process, the natural pigment can be prepared.

In the step of forming the matrix suspension, the matrix preferably has an average particle size of 2-250 μm and a thickness of 0.2-5 μm. If the average particle size is less than 2 μm, the matrix cannot exhibit a uniform color with a uniform refractive index due to light scattering resulting from a decrease in the aspect ratio, and if the average particle size is more than 250 μm, it will be difficult to form a coated oxide layer, due to an increase in the coated surface area.

Herein, when the amount of the matrix suspension is 100 parts by weight, the matrix is preferably contained in an amount of 3-15 parts by weight. If the content of the matrix is less than 3 parts by weight, the reaction efficiency will be reduced due to the too low concentration of the matrix, and if the content of the matrix is more than 15 parts by weight, aggregation will occur due to the high concentration of the matrix.

Herein, the stirring is preferably performed at room temperature and a speed of 200-500 rpm. If the stirring speed is less than 200 rpm, the dispersion effect will be reduced so that the pigment particles will aggregate, and if the stirring speed is more than 500 rpm, only the stirring speed (rpm) becomes higher without a further dispersion effect, resulting in a decrease in efficiency.

In the step of coating the flaky matrix, an inorganic salt solution is added to the matrix suspension to adjust the pH, followed by stirring, thereby forming an oxide layer on the surface of the flaky matrix.

Herein, the matrix may be a flaky matrix comprising one or more selected from among synthetic mica, natural mica, flaky glass, flaky iron oxide, flaky alumina, flaky silica, talc and bismuth, or may be a matrix comprising a metal oxide coated on the flaky matrix.

In this step, the pH may be adjusted by at least two pH adjustment steps.

The pH adjustment step comprises: a first pH adjustment step in which a 3-10 vol % metal salt solution is added slowly to the matrix suspension, followed by stirring for 5-30 minutes, thereby adjusting the pH to 7-7.1; a second pH adjustment step in which a 3-10 vol % metal salt solution is added slowly, followed by stirring for 5-30 minutes, thereby adjusting the pH to 4-4.1; a third pH adjustment step in which a 10-20 vol % HCl solution is added slowly, followed by stirring for 5-30 minutes, thereby adjusting the pH to 2.1-2.2; and a fourth pH adjustment step in which a 10-20 vol % basic solution is added slowly, followed by stirring for 5-30 minutes, thereby adjusting the pH to 4.2-4.4.

The preparation method further comprises, after the step of coating the flaky matrix, the steps of: washing and dehydrating the flaky matrix coated with the oxide layer; drying the washed flaky matrix; and screening a flaky matrix having a size larger than a desired size among the dried flaky matrix through a mesh.

The step of drying the flaky matrix may be performed at a temperature of 60° C. to 100° C. for 6-12 hours.

In the step of screening the flaky matrix, the separated flaky matrix has a particle size of 45 μm or less. In the screening step, aggregated particles formed during the reaction can be removed using a mesh sieve.

Method for Preparation of Red Pigment Coated with Metal Oxide

A red pigment coated with a metal oxide can be prepared by coating iron oxide ($Fe_2O_3$) as the metal oxide. A specific process for preparation of the red pigment is as follows.

First, a flaky matrix comprising one or more selected from among natural mica, synthetic mica, flaky alumina, flaky glass, flaky iron oxide, flaky silica, talc and bismuth is suspended in water (e.g., deionized water) at normal temperature (20 to 30° C.), and then stirred using a stirrer, thereby preparing a slurry.

After completion of the preparation of the slurry for preparing a pigment, the slurry is preferably heated to a temperature of 60-90° C. The reason why the slurry is heated in this manner is as follows. If the temperature of the slurry is lower than 60° C., the state of a coating layer to be formed later will not be uniform, and the size and shape of the material coated will be very irregular. If the temperature of the slurry is higher than 90° C., a coating for coating will intensively occur to form a rough coating layer. If the state of the coating layer formed on the matrix is unstable, the pigment will not have a high color saturation. For this reason, the above-described temperature range is preferably maintained.

After heating of the slurry is completed, a solution of an acid (e.g., hydrochloric acid (HCl)) is added to the slurry to adjust the pH of the slurry so that $FeCl_3$ can be hydrolyzed.

After completion of the slurry preparation, heating and pH adjustment processes, a step of forming a lower $Fe_2O_3$ coating layer is performed. In this step of forming the lower $Fe_2O_3$ coating layer, an $FeCl_3$ solution is added to the slurry such that the content of $FeCl_3$ in the slurry is 10-30 wt %, followed by titration. In the titration process, an aqueous solution of a base, for example, sodium hydroxide (NaOH) to 10-50%, is added to maintain the pH of the slurry at a constant value of 2.5-4.0.

If the content of $FeCl_3$ in the slurry is less than 10 wt %, the amount of the pigment that can be produced in a single process will be reduced, resulting in a decrease in productivity. If the content of $FeCl_3$ is more than 30 wt %, reactivity will be reduced, resulting in a non-smooth surface and an increase in impurities.

When a suitable pH is reached, $FeCl_3$ chloride (metal salt) in the $FeCl_3$ solution is hydrolyzed in an aqueous medium so that an $Fe_2O_3$ layer is coated on the surface of the flaky matrix. Herein, the $Fe_2O_3$ layer serves as a lower $Fe_2O_3$ layer.

Next, a $MgO.SiO_2$ solution is added to the slurry containing the lower $Fe_2O_3$ layer such that the content of $MgO.SiO_2$ in the solution is 2-20 wt %, followed by titration. In the titration process, a solution of an acid (e.g., hydrochloric acid) is added to maintain the pH of the slurry at a constant value of 5-9. Then, a solution of an acid (e.g., hydrochloric acid) is added again to adjust the pH of the slurry to 2.5-4.0, followed by reflux with stirring for about 10 minutes to 1 hour. Herein, if the content of $MgO.SiO_2$ is less than 2 wt %, the amount of the pigment that can be produced in a single process will be reduced, resulting in a significant decrease in productivity. On the contrary, if the content of $MgO.SiO_2$ is more than 20 wt %, reactivity will be reduced, resulting in a non-smooth surface and an increase in impurities. In addition, the pH value of the slurry is out of the above-specified range, coating of the $MgO.SiO_2$ layer will not be normally achieved, or the coated material will not be uniform and will have an irregular size and shape, so that the pigment will not have a high color saturation. When a suitable pH is reached, $MgO.SiO_2$ chloride in the $MgO.SiO_2$ solution is hydrolyzed in an aqueous medium to coat a $MgO.SiO_2$ layer on the surface of the lower $Fe_2O_3$ layer.

In a step of coating an upper $Fe_2O_3$ layer, a $FeCl_3$ solution is added to the slurry containing the $MgO.SiO_2$ layer such that the content of $FeCl_3$ in the solution is 10-30 wt %, followed by titration. In the titration process, an aqueous solution of a salt, for example, sodium hydroxide (NaOH) diluted to 10-50%, is added to maintain the pH of the slurry to 2.5-4.0, followed by reflux with stirring for about 10 minutes to 1 hour. The process of coating this upper $Fe_2O_3$ layer is performed in the same manner as the process of coating the lower $Fe_2O_3$ layer. When a suitable pH is reached, $FeCl_3$ chloride in the $FeCl_3$ solution is hydrolyzed in an aqueous medium to coat an $Fe_2O_3$ layer on the surface of the $MgO.SiO_2$ layer. Herein, the $Fe_2O_3$ layer serves as an upper $Fe_2O_3$ layer.

In the process ranging from the step of coating the lower $Fe_2O_3$ layer to the step of coating the upper $Fe_2O_3$ layer, the temperature of the slurry heated in the slurry preparation step is preferably maintained to stabilize the state of each coating layer.

Due to addition of the titration solution, the coating thickness of the metal oxide increases. The color of the metal oxide appears in the order of bronze, orange, copper, red and bluish red according to the thickness, and the reaction is stopped when a desired color appears. Particularly, because the metal oxide shows a high saturation when it is red, the reaction is advantageously stopped when that color appears.

In a step of obtaining an intermediate product, the slurry is stirred for about 10 minutes to 1 hour, and then the resulting slurry is filtered, dehydrated, washed several times with deionized water, and then dried at a temperature of about 80-150° C. for about 10-20 hours, thereby obtaining an intermediate product as the remaining material.

In a calcining step, the intermediate product obtained from the final slurry is calcined at a temperature of 600-900° C., thereby synthesizing a pigment. If the calcining temperature is lower than 600° C., the intermediate product will not be sufficiently calcined, and thus a desired pigment will not be obtained, and if the calcining temperature is higher than 900° C., the matrix will reach its melting point and melt, and thus a product that is not a desired pigment can be produced. The final pigment produced in this process comprises metal oxide layers having a stack structure of $Fe_2O_3$/$MgO.SiO_2$/$Fe_2O_3$ layers formed on the surface of the flaky matrix.

As described above, the pigment according to the present invention is prepared by a simple and cost-effective process, because the coating layer can be easily formed using the wet chemical process by hydrolyzing the metal salt in the aqueous medium.

Method for Preparation of Yellow Pigment Comprising Metal Oxide Coated on Flaky Glass A method for preparing a yellow pigment comprising a metal oxide coated on flaky glass is as follows.

First, glass flakes (e.g., 5 µm thick glass matrix) are added to and dispersed in water. Herein, the dispersion is preferably performed such that the content of the glass flakes is about 5-20 wt %. In addition, as the water, deionized water is preferably used in order to prevent ions from being adsorbed onto the glass flakes. The dispersion of the glass flake particles preferably has a temperature of 60 to 80° C.

Precursors of the metal oxide that is coated in the present invention are as follows. Precursors of tin dioxide include $SnCl_2$, and precursors of titanium dioxide include $TiCl_4$ ($TiOCl_2$ dissolved in aqueous solution), $TiOSO_4$, etc. In the process of adding the precursor, the pH of the dispersion is maintained at a suitable level, preferably 1.5-3. Specifically, hydrochloric acid is added to adjust the pH to 1.5-3, and then a metal oxide precursor is added to adsorb hydrated tin dioxide on the matrix, followed by adsorption of hydrated titanium dioxide. To adsorb the hydrated metal oxides, a basic aqueous solution such as sodium hydroxide is also added. In this process, it is important to add the metal oxide precursor while maintaining the above-described pH range.

After the adsorption reaction, a calcining process for forming a metal oxide is performed at a temperature of preferably 400 to 600° C. The calcining process is followed by a process in which aggregated particles formed during the reaction are removed by screening.

The pigment comprising the metal oxide coated on the glass flakes, prepared according to the above-described process, has a high glass due to the size of the particles and has a strong sparkling effect due to the thickness.

Method for Preparation of Blue Pigment Comprising Metal Oxide Coated on Synthetic Mica Particles A method for preparing a blue or violet pearlescent pigment comprising a metal oxide coated on synthetic mica particles is as follows.

First, synthetic mica particles are added to and dispersed in water such that the content of the particles is about 5-15 wt %. As the water, deionized water is preferably used in order to prevent ions from being adsorbed onto the particles.

The dispersion of the synthetic mica particles is heated to a temperature of 60-90° C., and then metal oxide precursors or mixtures thereof are added to the dispersion. Precursors of the metal oxide that is coated in the present invention are as follows. Precursors of tin dioxide include $SnCl_2$, and precursors of titanium dioxide include $TiCl_4$ ($TiOCl_2$ dissolved in aqueous solution), $TiOSO_4$, etc. In the process of adding the precursor, the pH of the dispersion is maintained at a suitable level, preferably 1-4. Specifically, an acid, preferably hydrochloric acid, is added to adjust the pH to 1-4, and then a metal oxide precursor is added to adsorb hydrated tin dioxide on the matrix, followed by adsorption of hydrated titanium dioxide. To adsorb the hydrated metal oxides, a basic aqueous solution such as sodium hydroxide is also added. In this process, it is important to add the metal oxide precursor while maintaining the above-described pH range.

When the tin dioxide ($SnO_2$) layer is pre-coated, a metal oxide coating layer having a rutile crystal structure can be formed. As the precursor is titrated into the dispersion, the coating thickness of the hydrated metal oxide increases, and the color of the hydrated metal oxide appears in the order of silver, yellow, red, blue and green according to the thickness. When the metal oxide reaches a desired color, the reaction is stopped. Particularly, because the metal oxide shows a high color saturation when it is violet and blue, the reaction is advantageously stopped when the two colors appear. The synthetic mica coated as described above is filtered, washed, dried and calcined to provide a product, and is finally screened. The processes following the coating step may be easily performed according to methods already known in the art.

Hereinafter, preferred examples for preparation of a pigment that is contained in a cosmetic composition according to the present invention will be described. It is to be understood, however, that these examples are presented as preferred examples and are not construed to limit the scope of the present invention in any way.

Contents that are not disclosed herein can be sufficiently understood by any person skilled in the art, and thus the description thereof is omitted.

EXAMPLES

Example 1

(1) Preparation of Red Natural Pigment

Natural dye extracted from *Caesalpinia sappan* (one or more selected from among *Caesalpinia sappan* bark extract and *Caesalpinia sappan* stem powder) that is a natural dye-containing material was heated in deionized water (or organic solvent) to extract a dye solution which was then concentrated and dried in a vacuum, thereby preparing dye. 10 parts by weight of the *Caesalpinia sappan* dye was added to a 2-L beaker, and 100 parts by weight and 30 parts by weight of $CaCl_2$ were added thereto, followed by stirring at 200 rpm. At this time, the reaction temperature was set at 40° C., and potassium hydroxide was added. The pH was adjusted to 7, and the solution was stirred. When a precipitate started to be formed during stirring, it was dehydrated, dried and powdered, thereby obtaining a pigment.

(2) Preparation of Red Natural Pigment Ink 140 parts by weight of deionized water and 60 parts by weight of the *Caesalpinia sappan* pigment were added to a 500 mL beaker, followed by milling at 70 rpm for 12 hours, thereby forming a *Caesalpinia sappan* pigment.

(3) Preparation of Pearlescent Pigment Comprising Red Natural Pigment Coated on Matrix Meanwhile, 100 parts by weight of metal oxide-coated flakes and 1000 parts by weight of deionized water were added to a 2 L beaker, and then dispersed at 400 rpm, thereby forming a matrix suspension. Herein, the reaction was performed at normal temperature.

The *Caesalpinia sappan* pigment was adjusted to a pH of 11 by adding potassium hydroxide thereto.

The matrix suspension, the *Caesalpinia sappan* pigment and $CaCl_2$ were added to a 2 L beaker, and the mixture solution was adjusted to a pH of 5.

After the *Caesalpinia sappan* pigment was coated on the flakes, stirring was performed for about 10 minutes, and then the reaction was terminated.

After coating with the red *Caesalpinia sappan* pigment, the resulting material was washed, dehydrated, and dried at 80° C., thereby preparing a red pearlescent pigment coated with the red *Caesalpinia sappan* pigment.

After completion of the drying process, aggregated particles formed during the reaction were removed by screening through a 325-mesh sieve.

Example 2

(1) Preparation of Yellow Natural Pigment

Natural dye extracted from *Gardenia florida* that is a natural dye-containing material was heated in deionized water (or organic solvent) to extract a dye solution. The extracted dye solution was concentrated and dried in a vacuum, thereby preparing dye. 20 parts by weight of the *Gardenia florida* dye was added to a 2 L beaker, and 100 parts by weight of deionized water and 30 parts by weight of $AlCl_3$ were added thereto, followed by stirring at 200 rpm. At this time, the reaction temperature was set at 60° C., and sodium hydroxide was added. The pH was adjusted to 7, and the solution was stirred. When a precipitate started to be formed during stirring, it was dehydrated, dried and powdered, thereby obtaining a pigment.

(2) Preparation of Yellow Natural Pigment Ink 140 parts by weight of deionized water and 60 parts by weight of the *Gardenia florida* pigment were added to a 500 mL beaker, followed by milling at 70 rpm for 12 hours, thereby forming a *Gardenia florida* pigment.

(3) Preparation of Pearlescent Pigment Using Yellow Natural Pigment

Meanwhile, 100 parts by weight of metal oxide-coated flakes and 1000 parts by weight of deionized water were added to a 2 L beaker, and then dispersed at 400 rpm, thereby forming a matrix suspension. Herein, the reaction was performed at normal temperature.

The *Gardenia florida* pigment was adjusted to a pH of 11 by adding potassium hydroxide thereto.

The matrix suspension, the *Gardenia florida* pigment and $CaCl_2$ were added to a 2-L beaker, and the mixture solution was adjusted to a pH of 5.

After the *Gardenia florida* pigment was coated on the matrix, stirring was performed for about 10 minutes, and then the reaction was terminated.

After coating with the yellow *Gardenia florida* pigment, the resulting material was washed, dehydrated, and dried at 80° C., thereby preparing a yellow pearlescent pigment coated with the yellow *Gardenia florida* pigment.

After completion of the drying process, aggregated particles formed during the reaction were removed by screening through a 325-mesh sieve.

Example 3

(1) Preparation of Blue Natural Pigment/Natural Pigment Ink

Natural dye extracted from *Indigo pulverata* that is a natural dye-containing material was heated in deionized water (or organic solvent) to extract a dye solution. The extracted dye solution was concentrated and dried in a vacuum, thereby preparing a pigment. 20 parts by weight of the *Indigo pulverata* pigment was added to a 250-ml ball milling bottle, and 80 parts by weight of deionized water was added thereto, followed by ball milling for 6 hours.

(2) Coating of Matrix with Blue Natural Pigment

Meanwhile, 30 parts by weight of metal oxide-coated flakes and 22.5 parts by weight of 20 vol % *Indigo pulverata* pigment were added to a 2-L beaker, and then deionized water was added thereto to a total volume of 500 parts by weight, and the mixture was dispersed at 400 rpm, thereby forming a matrix suspension. Herein, the reaction was performed at normal temperature.

A 5 vol % $AlCl_3$ solution was added slowly to the matrix suspension, followed by stirring for 10 minutes, thereby adjusting the pH of the suspension to 7.0. Next, 5 vol % $CaCl_2$ solution was added slowly, followed by stirring for 10 minutes, thereby adjusting the pH to 4.0. Then, 15 vol % HCl solution was added slowly, followed by stirring for 30 minutes, thereby adjusting the pH to 2.2. Finally, 15 vol % KOH solution was added slowly, followed by stirring for 30 minutes, thereby adjusting the pH to 4.3.

After the *Indigo pulverata* pigment was coated on the flakes, stirring was performed for about 10 minutes, and then the reaction was terminated.

After coating with the blue *Indigo pulverata* pigment, the resulting material was washed, dehydrated, and dried at 80° C., thereby preparing a yellow pearlescent pigment coated with the blue *Indigo pulverata* pigment.

After completion of the drying process, aggregated particles formed during the reaction were removed by screening through a 325-mesh sieve.

Example 4

Preparation of Pearlescent Pigment Comprising Metal Oxide Coated on Synthetic Mica 100 g of synthetic mica flakes having a particle size of 5-50 μm were added to 2 L of deionized water, and then stirred to form a slurry. Next, the slurry was heated to 75° C., and when it reached a temperature of 75° C., a HCl solution was added to adjust the pH of the slurry to 3.5.

Next, 600 g of a $FeCl_3$ solution ($FeCl_3$ content: 20.0 wt %) was added to the slurry at a constant rate over 5 hours while the pH of the slurry was maintained at a constant pH of 3.5 with a 10-50% NaOH dilution. After addition of the $FeCl_3$ solution, the slurry solution was refluxed for 10 minutes, and then adjusted to a pH of 6.8 by use of a 10-30% NaOH dilution.

Next, 400 g of a $MgO.SiO_2$ solution ($MgO.SiO_2$ content: 15.0 wt %) was added to the slurry at a constant rate over 2 hours while the slurry was maintained at a constant pH of 6.8 with a HCl solution. Thereafter, the slurry was adjusted to a pH of 3.5 by addition of a HCl solution, and then additionally stirred under reflux for 15 minutes.

Next, 570 g of a $FeCl_3$ solution ($FeCl_3$ content: 20.0 wt %) was added to the slurry at a constant rate over about 5 hours while the slurry was maintained at a pH of 3.5 with a 10-50% NaOH dilution. After addition of the $FeCl_3$ solution, the slurry was refluxed with stirring for 30 minutes. After reflux, the slurry was adjusted to a pH of 8.0-8.5 by addition of a 10-30% NaOH dilution, and then stirred under reflux for 30 minutes. After completion of the stirring, the resulting slurry was filtered, dehydrated, washed twice with deionized water, and dried at 120° C. for 10 hours, thereby obtaining an intermediate product as powder.

Finally, 11 g of the powder was calcined at 850° C. for 30 minutes to afford red pearlescent pigment powder.

Example 5

Preparation of Yellow Pigment Comprising Metal Oxide Coated on Glass Flakes 50 parts by weight of glass flakes having a particle size ranging from 40 μm to 250 μm and a thickness of 5 μm were added to a 2 L beaker, and then deionized water was added thereto to a total weight of 1000 parts by weight. Then, the flakes were dispersed at 300 rpm to form a matrix suspension.

Next, the matrix suspension was heated to 75° C., and 5% hydrochloric acid solution was added to adjust the pH of the matrix suspension to 1.9. Then, 20 ml of a 11% $SnCl_4$ solution was added to the matrix suspension while the pH of the matrix suspension was maintained at a pH of 1.9 with 20% NaOH solution.

After addition of the $SnCl_4$ solution, the suspension was stirred for 30 minutes, and then 100 ml of 20% $TiCl_4$ solution was added to the suspension while the pH of the suspension was maintained at a pH of 1.9 with a 20% NaOH solution.

After completion of the reaction, the resulting solution was stirred for 30 minutes, and then washed and dehydrated twice, followed by drying at 90° C. for 2 hours.

The dried material was calcined at 550° C. for 30 minutes, and then aggregated particles formed during the reaction were removed by screening through a 200-mesh sieve.

Example 6

Preparation of Blue Pearlescent Pigment Comprising Metal Oxide Coated on Synthetic Mica Particles To prepare a blue pearlescent pigment comprising a metal oxide coated on synthetic mica particles, synthetic mica was powdered and sieved, thereby obtaining synthetic mica particles having an average particle size of 12 μm. 100 parts by weight of the synthetic mica particles were added to a beaker, and then deionized water was added thereto to a total weight of 1000 parts by weight. Then, the mica particles were dispersed at 300 rpm to form a matrix suspension. Next, the matrix suspension was heated to 80° C.

The matrix suspension was adjusted to a pH of 2.2 using a 5% hydrochloric acid solution, and then refluxed for 10 minutes. Next, 30 ml of a 30% $SnCl_2$ solution was added to the matrix suspension while the pH of the suspension was maintained at 2.2 with a 20% NaOH solution.

After addition of the $SnCl_2$ solution, the suspension was stirred for 30 minutes, and then 120 ml of a 40% $TiOCl_2$ solution was added to the suspension while the pH of the suspension was maintained at 2.2 with a 20% NaOH solution.

After addition of the $TiOCl_2$ solution, the suspension was refluxed for 10 minutes, and then adjusted to a pH of 8 by addition of a 20% NaOH aqueous solution. Next, the suspension was adjusted to a pH of 1.7 by addition of a 10% HCl aqueous solution, and then $SnCl_2$ and $TiOCl_2$ aqueous solutions were added to the suspension under the same conditions as described above. It was observed that the color changed in the order of yellow, red, violet and blue according to the thickness of the titanium dioxide, and the reaction was stopped when the color reached blue.

After completion of the reaction, the reaction solution was stirred for 30 minutes, and then washed and dehydrated twice, followed by drying at 100° C. for 2 hours. The dried material was calcined in an electric furnace at 800° C., thereby obtaining a blue pigment showing a high color saturation. Next, aggregated particles formed during the reaction were removed by screening through a 325-mesh sieve.

Application Examples

The pearlescent pigments prepared according to the Examples of the present invention may be used as pigments in cosmetic products, including mascara, eyeshadow, eyeliner (liquid or gel), and nail enamel.

Tables 1 to 5 below show the compositions of mascara, eyeshadow, liquid eyeliner, gel-type eyeliner and nail enamel, which contain the pigment preparing to the Example of the present invention.

TABLE 1

| Component | Content |
|---|---|
| Cetearyl alcohol | 2.00 |
| PEG 20 glyceryl stearate | 1.50 |
| Beeswax | 11.00 |
| Stearic acid | 8.00 |
| Black iron oxide | 3.00 |
| Preservative | 0.50 |
| Pearlescent pigment | 7.00 |
| Butylene glycol | 2.00 |
| Acrylate copolymer | 30.00 |
| Polyvinyl alcohol | 3.00 |
| Triethanolamine | 3.00 |
| Purified water | 29.00 |
| Sum | 100.00 |

Table 1 above shows the composition of a mascara comprising the pigment prepared according to the Example 1.

TABLE 2

| Component | Content |
|---|---|
| Pearlescent pigment | 10.0 |
| Talc | 68.40 |
| Mica | 7.20 |
| Zinc stearate | 5.40 |
| Silica | 4.50 |
| Methylmethacrylate copolymer | 2.88 |
| Titanium dioxide | 1.44 |
| Aluminum stearate | 0.09 |
| Triethoxycaprylylsilane | 0.05 |
| Dimethicone | 0.04 |
| Sum | 100.00 |

Table 2 above shows the composition of an eyeshadow comprising the pigment prepared according to Example 2.

TABLE 3

| Component | Content |
|---|---|
| Purified water | 32.87 |
| Butylene glycol | 1.00 |
| Sodium polyacrylate | 1.00 |
| Disodium EDTA | 0.03 |
| Black iron oxide | 10.00 |
| Pearlescent pigment | 14.00 |
| Silica | 0.50 |
| Preservative | 0.30 |
| Silicone oil | 2.00 |
| Caprylic/capric triglyceride | 2.00 |
| Diisostearyl maleate | 2.00 |
| Cetearyl olivate/sorbitan olivate | 2.00 |
| Polyoxyethylene lauryl ether | 2.00 |
| Preservative | 0.30 |
| Acrylate copolymer | 30.00 |
| Sum | 100.00 |

Table 3 above shows the composition of a liquid eyeliner comprising the pigment prepared according to Example 3.

TABLE 4

| Component | Content |
|---|---|
| Ceresin | 18.00 |
| Sodium polyacrylate | 3.00 |
| Silicone acrylate | 2.00 |
| Cyclomethicone | 10.70 |
| Silicone oil | 3.00 |
| Preservative | 0.30 |
| Isodecane | 10.00 |
| Caprylic/capric triglyceride/stearalkonium hectorite/propylene carbonate | 33.00 |
| Pearlescent pigment | 20.00 |
| Sum | 100.00 |

Table 4 above shows the composition of a gel-type eyeliner comprising the pigment prepared according to Example 4.

TABLE 5

| Component | Content |
|---|---|
| Pearlescent pigment | 3.00 |
| Nitrocellulose (½ sec) | 10.00 |
| Alkyd resin | 10.00 |
| Acetyl tributyl citrate | 2.00 |
| Ethyl acetate | 20.00 |
| Butyl acetate | 15.00 |

TABLE 5-continued

| Component | Content |
|---|---|
| Ethyl alcohol | 5.00 |
| Toluene | 35.00 |
| Sum | 100.00 |

Table 5 above shows the composition of a nail enamel comprising the pigment prepared according to Example 5.

The characteristics (including spreadability, hiding power, color and matte feeling) of the mascara, eyeshadow, liquid eyeliner, gel-type eyeliner and nail enamel prepared according to the compositions shown in Tables 1 to 5 above are shown in Table 6 below.

TABLE 6

| | Kind of cosmetic | Spreadability | Hiding power | Color | Matte feeling |
|---|---|---|---|---|---|
| Example 1 | Mascara | ☉ | ☉ | ⊚ | ☉ |
| Example 2 | Eyeshadow | ⊚ | ☉ | ⊚ | ⊚ |
| Example 3 | Eyeliner (liquid) | ☉ | ⊚ | ☉ | ⊚ |
| Example 4 | Eyeliner (gel) | ☉ | ☉ | ⊚ | ☉ |
| Example 5 | Nail enamel | ☉ | ☉ | ⊚ | ⊚ |

X (score of less than 60): poor;
Δ (score of 60-69): moderate;
○ (score of 70-79): relatively good;
⊚ (score of 80-89): excellent;
☉: (score of 90-100): very excellent.

To evaluate the spreadability, hiding power, color and matte feeling of each cosmetic product, sensory evaluation of each cosmetic product (score: 0 to 100) was performed by 40 women panels (aged 20 to 40 years), and the evaluation scores were averaged. The results of the evaluation are shown in Table 6 above.

Referring to Table 6 above, it can be seen that, when the pigment prepared in the Example is used as a cosmetic pigment, it shows excellent spreadability, hiding power, transparency and color. This suggests that the pearlescent pigment according to the present invention can exhibit performance equal to or higher than cosmetic pigments that are conventionally used.

Although the preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A cosmetic composition, comprising:
a pigment, wherein the pigment comprises:
  a matrix; and
  a mixture of a vegetable natural pigment and a metal coated on the matrix;
a resin; and
a solvent,
wherein the cosmetic composition is capable of exhibiting various colors,
wherein the mixture of the vegetable natural pigment and the metal is coated on the matrix by co-precipitating a dye/metal salt mixture solution comprising:
  water;
  the vegetable natural pigment, wherein an amount of the vegetable natural pigment ranges from 3 parts by weight to 30 parts by weigh based on 100 parts by weight of the water; and
  a metal salt, wherein an amount of the metal salt ranges from 3 parts by weight to 30 parts by weigh based on 100 parts by weight of the water, and the metal salt is at least one selected from the group consisting of $BaCl_2$, $CaCl_2$, $AlCl_3$, $SnCl_4$, $TiCl_4$, $TiOCl_2$, $TiOSO_4$, $FeCl_3$, $FeSO_4$, $SiCl_4$, $ZrOCl_2$, $Na_2O.SiO_2.5H_2O$, $MnCl_2$, $MgCl_2$ and $CoCl_2$, and
wherein the dye/metal salt mixture solution is co-precipitated by introducing a basic solution into the dye/metal salt mixture.

2. The cosmetic composition of claim 1, wherein the pigment is contained in an amount of 2-50 wt % based on the total weight of the composition.

3. The cosmetic composition of claim 1, wherein the cosmetic is an oily cosmetic composition in which the solvent is oil and the resin is an oil-soluble resin.

4. The cosmetic composition of claim 1, wherein the cosmetic composition is an aqueous cosmetic composition in which the solvent is water and the resin is a water-soluble resin.

5. The cosmetic composition of claim 1, wherein the matrix is coated with a metal oxide.

6. The cosmetic composition of claim 5, wherein the metal oxide comprises one or more of iron oxide, titanium dioxide and tin dioxide.

7. The cosmetic composition of claim 1, wherein the cosmetic composition is a composition for mascara, eyeshadow, liquid eyeliner, gel-type eyeliner, nail enamel, foundation, lipstick, lip gloss, cosmetic cream, makeup foundation, eye pencil, blusher, or emulsion.

8. The cosmetic composition of claim 1, wherein the matrix is at least one selected from the group consisting of synthetic mica, natural mica, flaky glass, flaky iron oxide, flaky alumina, flaky silica, talc, and bismuth.

9. The composition of claim 1, wherein the matrix is at least one selected from the group consisting of flaky iron oxide, talc, and bismuth.

10. The composition of claim 1, wherein the vegetable natural pigment is derived from at least one selected from the group consisting of *Caesalpinia sappan*, *Gardenia florida*, *Indigo pulverata*, indigo, *Commelina communis*, iris, madder, safflower, *sappan* wood, logwood, gromwell, persimmon, apricot trees, plum trees, Korean spindle trees, ginger trees, radix *Euphorbiae kansui*, *Althaea rosea*, *Polygonum cuspidatum*, wild apricot trees, *Taxus cuspidata*, *Schizandra chinensis*, *camellia*, grapes, brush trees, *gardenia*, *Curcuma longa*, onion peels, *Carthamus* yellow, *Coptis japonica* root, *Phellodendron amurense* bark, clove, pomegranate, reed, *Sophorae flus*, *Fraxinus rhynchophylla*, *Rhus verniciflua*, old trees, *Sorbus alnifolia*, garden-bell tree bark, *wisteria* flowers, alders, chestnuts, and oak trees.

* * * * *